United States Patent [19]

Schlesselman et al.

[11] 4,225,842
[45] Sep. 30, 1980

[54] RESISTANCE TYPE OXYGEN SENSOR

[75] Inventors: Harold D. Schlesselman, Fostoria; David C. Weber, Toledo, both of Ohio

[73] Assignee: Bendix Autolite Corporation, Fostoria, Ohio

[21] Appl. No.: 60,268

[22] Filed: Jul. 25, 1979

[51] Int. Cl.³ .............................................. H01L 7/00
[52] U.S. Cl. ..................................... 338/34; 73/27 R; 73/23; 422/98
[58] Field of Search ................... 338/34; 73/23, 27 R; 23/232 E; 422/98; 324/65 P, 718 N; 340/632, 634

[56] References Cited

U.S. PATENT DOCUMENTS

| | | | |
|---|---|---|---|
| 4,001,758 | 1/1977 | Esperg et al. | 338/34 |
| 4,007,435 | 2/1977 | Tien | 338/34 |
| 4,088,555 | 5/1978 | Kita et al. | 204/195 S |
| 4,101,404 | 7/1978 | Blumenthal et al. | 204/195 S |
| 4,147,513 | 4/1979 | Bienkowski et al. | 73/23 X |

Primary Examiner—C. L. Albritton
Attorney, Agent, or Firm—William G. Kratz, Jr.; Raymond J. Eifler

[57] ABSTRACT

A temperature compensated oxygen sensor has a generally cylindrical first insulator with an axial bore extending therethrough which is counterbored at one end. A second cylindrical insulator is retained in the bore in the first insulator either by a radial inwardly directed flange on the second end of the first insulator or by a radial outwardly directed flange on one end of the second insulator which seats in the counterbore of the first insulator. A titania resistor and a compensating resistor are mounted on the second end of the second insulator by leads extending through longitudinal bores in a second cylindrical insulator and into the counterbore in the first insulator. The leads are connected to terminals which are retained in the counterbore either by a chemical bonding agent or by a third cylindrical insulator through which the terminals extend. The third insulator can be secured either by mechanical means and/or by a chemical bonding agent including a glass preform.

21 Claims, 13 Drawing Figures

RESISTANCE TYPE OXYGEN SENSOR

FIELD OF THE INVENTION

This invention relates to resistance type gas sensors and, more particularly, to sensors of this type used to determine the oxygen concentration in the exhaust gases of internal combustion engines.

PRIOR ART

Exhaust gas sensors which exhibit changes in electrical resistance proportional to the partial pressure of oxygen present in the gas to which the sensor is exposed are well known. Titania ceramic material, for instance, is used in such sensors. It is known that the electrical resistance of the titania ceramic material varies with temperature as well as with the partial pressure of oxygen. It is also known that the temperature versus electrical resistance characteristics of various materials closely follow those of titania. These materials are called thermisters or compensators. As a consequence, the titania sensor can be compensated for temperature variations by exposing both the titania element and a temperature compensating resistor to the test gas and electrically canceling the change in resistance due to temperature in the manner taught by U.S. Pat. No. 4,147,513.

A practical problem in commercially producing gas sensors is to provide a structure which will have a long, maintenance free life in the environment for which it is designed and which can be manufactured easily and inexpensively. Since the temperature compensated titania sensor has both titania and compensator resistors, four electrical leads, or three if a common ground is used, are required for connecting the elements to appropriate external electronic circuitry. A significant portion of the cost of these sensors is attributable to the platinum wires that are used for the electrical leads. Platinum is used for these leads because of its ability to withstand the high temperatures and corrosive atmosphere to which the sensor elements are exposed.

The temperature compensated titania sensor disclosed in U.S. Pat. No. 4,147,513 includes a unitary, cylindrical ceramic insulator having a recess in one end in which are located the titania and compensating resistors. The platinum wire leads extend through three longitudinal bores in the ceramic insulator and through axial bores in terminals which are cemented in counterbores in the opposite end of the insulator. The leads are silver soldered to the free ends of the terminals which may be plugged into a suitable socket connected to the analyzer circuitry. The sensor is mounted in the wall of the exhaust system of an internal combustion engine by a threaded, annular, metallic shell which is crimped around an enlarged portion of the cylindrical ceramic insulator.

While this currently used sensor is quite satisfactory in its performance, seven distinct manufacturing steps are required to fabricate the unitary ceramic insulator. Furthermore, the unit is difficult to assemble and the long lengths of platinum wire required for the leads add to the cost of the sensor.

The primary object of the present invention is to provide a resistance type oxygen sensor which is easy to assemble and can be constructed at a reasonable cost.

It is a subsidiary object to provide a sensor as set forth in the previous object which uses a minimum amount of platinum wire.

It is also an object of the invention to provide such a sensor in which major parts can be extruded or pressed and need only be trimmed to length.

SUMMARY OF THE INVENTION

While it would normally be expected that a sensor could be made more easily and inexpensively by constructing it of fewer parts, applicants have found that in the case of the resistance type oxygen sensor, these results can be achieved by breaking the sensor down into more parts which are themselves easier and more inexpensive to produce and then assembling them into the finished product. Thus, the sensor of this invention includes a first generally cylindrical electrical insulator (1) having an axial bore (3) extending therethrough which is counterbored (9) at one end. An annular connector shell (33) fits over and engages a radially enlarged portion (11) of the first insulator (1) spaced from the second end of the insulator (1) and is adapted to be secured in the wall of the exhaust system with the second end of the insulator (1) projecting into the exhaust gas stream.

A second electrical insulator (13) of uniform circular cross-section is disposed in the bore (3) of the first insulator (1) with a first end thereof adjacent the counterbore (9). The second insulator (13) is retained in the bore (3) either by a radial inwardly directed flange (5) on the second end of the first insulator (1) or by a flange (71) affixed to the first end of the second insulator (13) which seats in the counterbore (9) of the first insulator (1). This flange (71) may be affixed to the second insulator (13) in several ways with the preferred arrangement being to apply a green slip of the same ceramic material to an extruded green insulator (13) and firing the resulting assembly.

The second insulator (13) is provided with two, three or four longitudinal bores (15) depending upon the sensor materials being used and whether or not a common ground is employed. In the case of the temperature compensated titania sensor, the titania resistor (17) and compensating resistor (19) is secured to the second end of the second insulator (13) by platinum leads (21) extending individually through the longitudinal bores (15) in the second insulator (13) and into the counterbore (9) in the first insulator (1). The free end of each platinum lead (21) is silver soldered or welded to one end of a terminal (25) which extends axially out of the counterbore (9) in the first insulator (1).

The terminals (25) are secured in the counterbore (9) in one of two ways. First, they may be cemented in place by filling the counterbore with an electrically nonconductive sealing material (31) such as a cement, caulk or glass refractory bonding agent. If this method of securing the terminals (25) is used, the counterbore (9) may comprise a longitudinal bore (45) for each terminal which is offset radially from but intersects the axial bore (3a) in the first insulator (1a).

The second means for securing the terminals in the counterbore includes a third cylindrical, electrical insulator (29) which slides into the counterbore (9) and is provided with a plurality of longitudinal bores (27) through each of which a terminal (25) extends. This third insulator (29, 29b) may be secured in the counterbore (9) either by chemical bonding agents such as the cement, caulk or glass refractory bondagent (31) mentioned above, or by mechanical means such as by a force fit or by crimping the annular, metallic shell (33b) over the end of the first insulator (1b). In addition, a glass preform can be placed in the counterbore (9) under the third insulator (29) and the assembly sealed by applying heat to the exterior of the first insulator (1) to soften the preform while pressing down on the third insulator (29). The terminals (25) may be chemically bonded in the bores in the third insulator (29) and/or they may be provided with enlarged inner ends (23) to which the platinum leads (21) are electrically secured and which are larger in diameter than the bores (27) in the third insulator (29).

With the above arrangement, the length of the platinum leads (21) is kept to a mininum, the first insulator (1) may be pressed automatically on isostatic presses to exact internal dimensions and the second (13) and third insulators (29) can be extruded or pressed from ceramic material and need only be trimmed to length. The sensor is assembled by inserting the platinum leads (21) through the bores (15) in the second insulator (13), and soldering or welding the free ends to the terminals (25). The third insulator (29), if used, is then slid over the terminals (25) and coated with or attached with a preform of a bonding agent (31), if used, and the unit is inserted into the first insulator (1) from the counterbored end (9). If a bonding agent (31) is not used, the end (49) of the annular shell (33b) is crimped over the end of the third insulator (29) to lock it in place. Alternatively, the third insulator (29) is press-fitted in the end of the first insulator (1). If the third insulator (29) is not used, the chemical bonding agent (31) is inserted in the counterbore (45) to secure the terminals (25a).

Various configurations of the first (1) and third (29) insulators are possible and, in addition, the sensor may be provided with a key (53 or 57) or a keyway (43, 43a, 51, 65, 65f or 65g) for proper mating of the terminals (25) with a connector plug. Furthermore, the flanged end of the insulator (1) may be provided with a perforated metallic shield (41) or a press-fit perforated ceramic disc (67) or the end of the insulator (1g) may be formed with a single small bore (71) to protect the sensor elements (17, 19) from bombardment by particulates in the gas stream.

DESCRIPTION OF THE PREFERRED EMBODIMENTS

Figure 2:
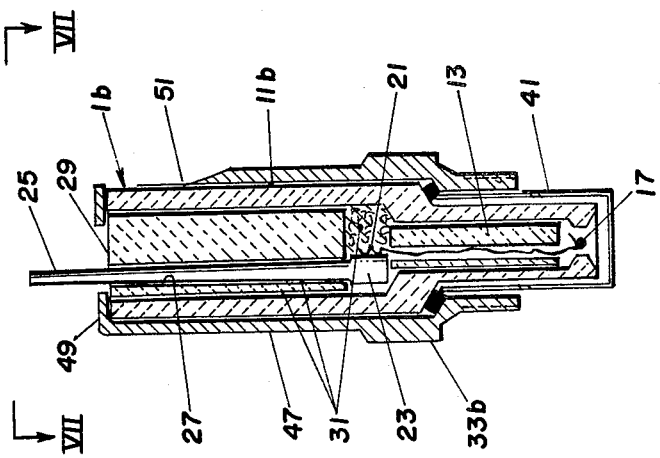
FIG. 2 is a top end view of the sensor of FIG. 1.
Figure 3:
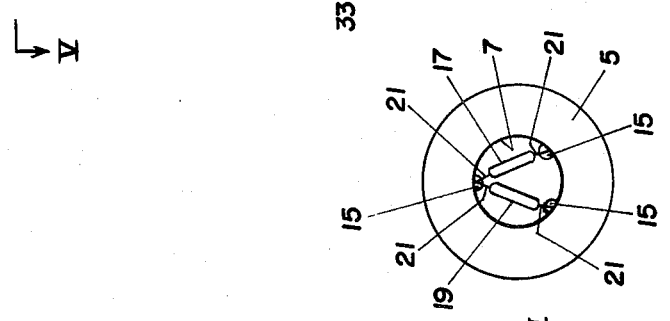
FIG. 3 is a bottom end view of the sensor of FIG. 1.
Figures 1, 4, 6:
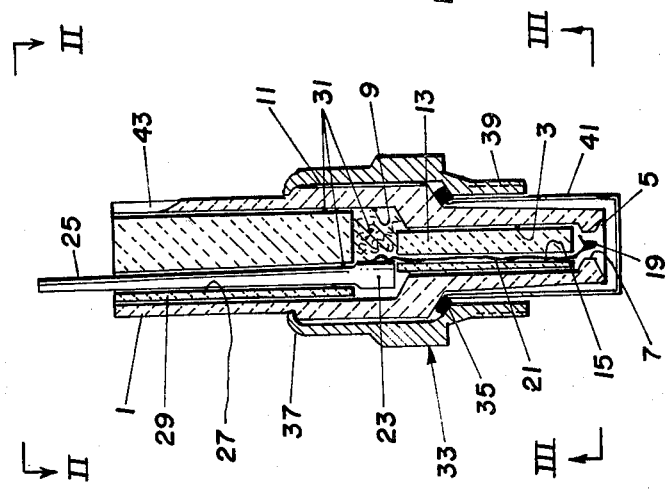
FIG. 1 is a longitudinal section taken through a sensor in accordance with one embodiment of the invention.
FIG. 4 is a longitudinal section taken through a sensor in accordance with a second embodiment of the invention.
FIG. 6 is a longitudinal section taken through a sensor in accordance with a third embodiment of the invention.

FIGS. 1 through 3 illustrate a sensor made in accordance with the teachings of the invention and in which the first insulator 1 is an elongated, generally cylindrical member having an axial bore 3 extending the length thereof. A radial inwardly directed and inwardly tapered flange 5 on one end of the insulator 1 forms an aperture 7. The opposite end of the bore 3 is provided with a counterbore 9. A portion of the insulator 1 spaced from the flanged end is radially enlarged as at 11. The insualtor 1 can be readily formed with exact internal dimensions from electrically insulating ceramic materials on isostatic presses in a well known manner. Any ceramic material offering good thermal shock resistance, high electrical resistance, good mechanical strength and a hermetic seal may be used in fabricating the insulator 1. Alumina (88%) is one such suitable material.

A second electrical insualtor 13 of cylindrical form is received in the bore 3 of the first insulator where it bears against the flange 5 and extends substantially to the counterbore 9. This second insulator 13 is provided with three longitudinal bores 15 which provide communication between the aperture 7 and the counterbore 9. The insulator 13 may be extruded or pressed from the same type of electrically nonconductive ceramic material as the insulator 1. The only finishing required is to trim the insulators to length.

A titania resistor 17 and a compensating resistor 19 are mounted in the aperture 7 by platinum electrical leads 21 which extend through the bores 15 into the counterbore 9. The lead 21 at one end of the titania resistor 17 is soldered to the lead from one end of the compensating resistor 19 to form a common lead which extends through one of the bores 15, thereby reducing the amount of platinum wire required. The ends of the leads 21 which extend into the counterbore 9 are silver soldered or welded to the enlarged inner ends 23 of terminals 25. The compensating resistor may be composed of stabilized zirconia or other suitable materials such as those set forth in U.S. Pat. No. 4,147,513.

The terminals 25 extend through longitudinal bores 27 in a third insulator 29 and project beyond the end of this insulator which terminates flush with the end of insulator 1. Insulator 29 is fabricated in a manner similar to that discussed above in connection with insulator 13 and from similar materials. The insulator 29 is retained in the counterbore 9 by a chemical bonding agent 31 such as cement, caulk or a glass refractory bonding agent. The same material can be used to fill the cavity at the bottom of the counterbore around the enlarged ends of the terminals and to seal the terminals in the bores 27. Alternatively, a glass preform can be used as the bonding agent.

An annular, metallic connector shell 3 slides onto the flanged end of insulator 1 to bring a shoulder 35 on the connector into contact with the lower edge of the enlarged portion 11 of the connector. The leading edge 37 of the connector is crimped over the other edge of the enlarged portion 11 to secure the connector shell to the insulator 1. The connector shell 3 is threaded as at 39 for installing the sensor in the wall of the exhaust system of an internal combustion engine or other gas stream that is to be analyzed for oxygen concentration. An integral hexagonal center section 39 of the connector shell is adapted to be engaged by a suitable tool for installing or removing the sensor.

The working end of the sensor may be provided with a metallic cup-shaped shield 41 which is clamped onto the flanged end of the sensor by the shoulder 35 on the connector shell 33. The shield 41 is perforated to allow the gases to reach the resistors 17 and 19 while screening out the particulates in the gas stream which would reduce the life of the resistors.

The terminals 25 are adapted to be received in a plug (not shown) which is connected to a suitable gas analyzer circuit such as that shown in U.S. Pat. No. 4,147,513. A keyway 43 extending longitudinally from the upper end of the first insulator 1 assures that the terminals 25 are properly mated with the leads in the electrical plug.

In assembling the sensor of FIGS. 1 through 3, the platinum leads 21 are fed through the longitudinal bores 15 in the sencond insulator 13 and silver soldered or welded to the enlarged ends 23 of the terminal posts 25. This subassembly is then inserted into the bore 3 of the first insulator 1. The chemical bonding agent 31 is then injected into the bottom of the counterbore 9 and before it sets, bores 27 in the third insulator 29 are injected with the bonding agent, aligned with the terminals 25 and seated within the counterbore 9 as shown in the Figures. When a glass preform is used, localized heat is applied to the exterior of the shell 3 to soften the preform and then the third insulator 29 is pressed into the counterbore 9 to cause the glass to flow and effect the seal. Next, the shield 41 is placed over the flange end of the insulator 3 and, finally, the connector shell slides over the shield and is secured in place by crimping the edge 37.

As can be seen from FIGS. 1 through 3, the disclosed sensor shortens the length of the platinum leads and is easily assembled from readily fabricated components.

Figure 5:
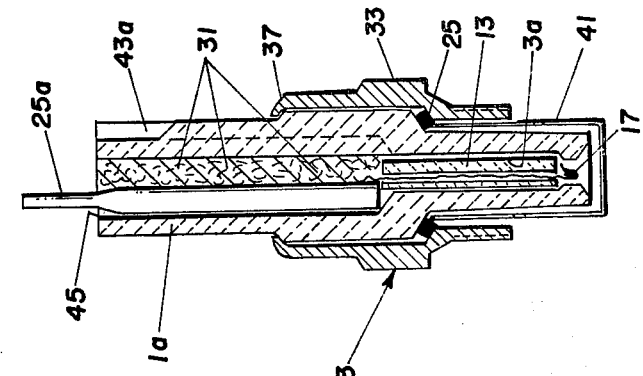
FIG. 5 is a top end view of the sensor of FIG. 4.

FIGS. 4 and 5 illustrate another embodiment of the invention wherein components identical to those in the sensor of FIGS. 1 through 3 are given like reference characters. In the sensor, the counterbore in the first insulator 1a comprises 3 longitudinal bores 45 which are radially offset from, but partially intersect, the axial bore 3a. The terminal posts 25a which are silver soldered or welded to the leads 15 at their lower ends are seated in the bores 45 and secured in place by a chemical bonding agent 31. The insualtor 1a is again provided with a longitudinal keyway 43a and in other respects the sensor of FIGS. 4 and 5 is the same as that of FIGS. 1 through 3.

Figure 7:
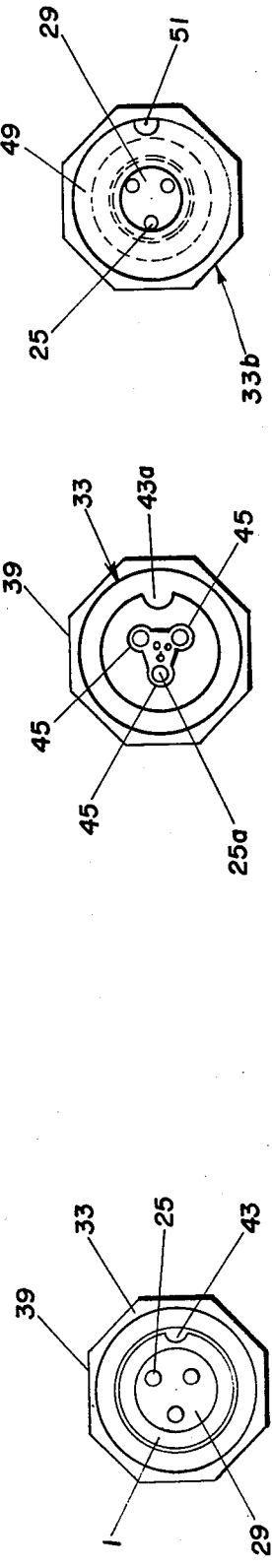
FIG. 7 is a top plan view of the sensor of FIG. 6.

The sensor of FIGS. 6 and 7 is similar to that of FIGS. 1 through 3 except that the radially enlarged portion 11b of the first insulator 1b extends all the way to the upper end of the first insulator and the longitudinal keyway 43 is not provided in the insulator. In addition, the annular wall 47 of the connector shell 43b extends to the end of the insulator 1b and terminates in a radial inwardly directed flange 49 which extends over the end of the third insulator 29 and retains it in place. The flange 49 is formed after the internal parts are assembled by crimping the end of the wall 47. Actually, this sensor is held together by the mechanical arrangement; however, a chemical bonding agent 31 can also be used in the same areas as in the first sensor which assures that no gases leak through the sensor. In this arrangement, the longitudinal keyway 51 is provided in the shell 33b.

The sensor of FIG. 3 is similar to that in FIGS. 6 and 7 except that the first insulator 1c does not extend appreciably toward the terminal end of the sensor from the enlarged portion 11c. Instead, the third insulator 29 just seats in the end of the counterbore 9c and is held in place by the annular wall 47c of the connector shell 33c and the radial inwardly directed flange 49c which is crimped over the end of insulator 49. In addition, this sensor is provided with a longitudinal key 53 in the wall 47c of the connector shell rather than a keyway.

Figures 8, 9, 10:
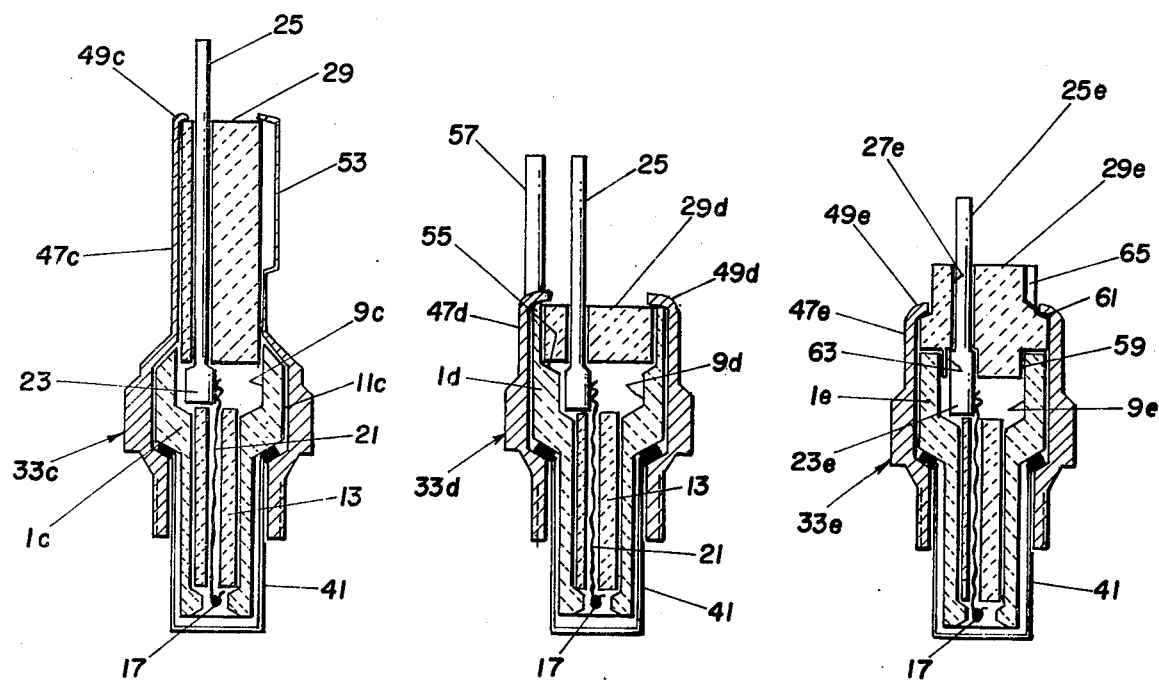
FIGS. 8 through 13 are longitudinal sections taken through sensors in accordance with additional embodiments of the invention.

The sensor shown in FIG. 9 is similar to the sensor of FIGS. 6 and 7 except that the counterbored portion of the first insulator 1d is shortened but not as much as in the sensor of FIG. 8. The third insulator 29d is also shortened so that it fits fully within the counterbore 9d of the first insulator and is held in place by the crimped flange 49d on the annular wall 47d of the connector shell 33d. The counterbore 9d is stepped with the third insulator 29d seated on a shoulder 55 in the counterbore. A bayonet type key 57 projects from the connector shell 33d parallel to the terminals 25.

The embodiment of the invention shown in FIG. 10 is similar to that of FIG. 9 in that again the counterbored portion of the first insulator 1e is shortened; however, the counterbore is not stepped. Instead, the third insulator is rabbeted as at 59 to mate with the end of insulator 1e. The free end of insulator 29e is provided with an annular recess 59 forming a shoulder 61 around which the annular wall 47e of the connector shell 33e is crimped as at 49e. The inner ends of longitudinal bores 27e are counterbored as at 63 to receive the extended enlarged ends 23e of the terminals 25e and the exposed end of the insulator 29e is provided with a longitudinal keyway 65.

Figure 11:
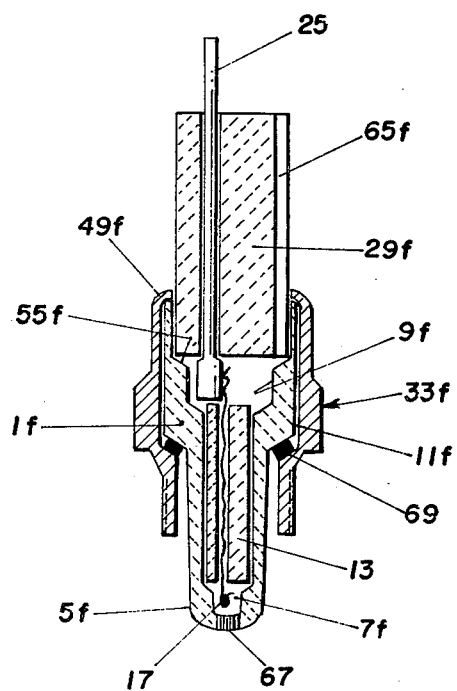

FIG. 11 illustrates yet another embodiment of the invention in which the first insulator 1f is similar at its counterbored end to the insulator 1d in FIG. 9. However, in this arrangement the third insulator 29f, which abuts the shoulder 55f in the stepped counterbore 9f, extends a substantial distance beyond the end of insulator 1f and is provided with a longitudinal keyway 65f and the sidewall 47f of the connector shell 33f is only crimped over and engaged the end of the first insulator as at 49f. In addition, the flange 5f on the end of the insulator 1f is axially extended and a perforated ceramic disc is pressed into the end of aperture 7f. The perforated disc 67 protects the sensing resistors from particulates while eliminating the need for the perforated metallic shield 41. An annular gasket 69 is inserted between the connector shell 33f and the radially enlarged portion 11f of the first insulator to prevent leakage of exhaust gases through this area.

Figure 12:
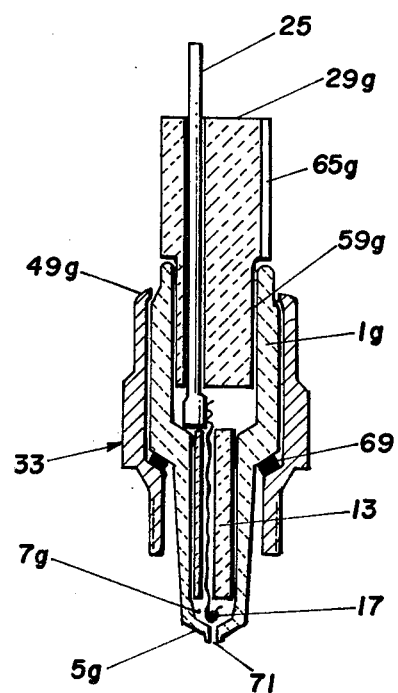

FIG. 12 illustrates an embodiment of the invention in which the third insulator 29g is rabbeted into the first insulator 1g for a substantial distance as at 59g and extends for a substantial distance beyond the end of the insulator 1g. Only the insulator 1g is held in place by the crimped end 49g of the connector shell 33. The insulator 29g is secured by a press-fit or a chemical bonding agent. The insulator 29g is provided with an elongated longitudinal keyway 65g. This sensor also eliminates the need for a metallic shield to protect the sensing resistors from particulates by providing a stepped flange 5g which extends radially inward and then axially outward to leave but a narrow opening 71 into the aperture 7g where the sensing resistors are located. As in the case of the sensor of FIG. 11, a gasket 69 is provided between the connector shell 33 and the first insulator 1g to prevent leakage of exhaust gases out of the exhaust system.

Figure 13:
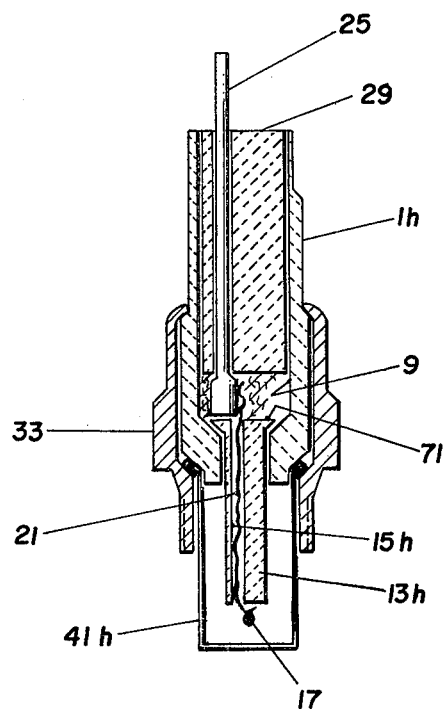

FIG. 13, discloses yet another embodiment of the invention in which the second insulator 13h extends beyond the end of the first insulator 1h. Thus the insulator 1h is not provided with a radial inwardly directed flange as in the other embodiments of the invention and the second insulator is held within the insulator 1h by radial outwardly directed flange 71 on the inner end of insulator 13h which seats in the counterbore 9 of the first insulator 1h. This flange 71 may be affixed to the second insulator 13h in various ways. A preferred procedure is to paint spray or dip into a green extruded second insulator 13h a green slip of the same ceramic material and to fire the resulting assembly. Alternatively, a ceramic ring of the same material can be cemented onto the end of the second insulator 13h using a refractory cement or a ring of refractory cement can be brushed, sprayed or dipped onto the insulator. Other possible ways of affixing the flange 71 to the second insulator include: green machining an oversized insulator to form the flange at one end and firing a green ceramic ring onto the insulator. The resistors 17 and 19 mounted on the end of the second insulator by the platinum leads 21, while not recessed in the end of the first insulator 1h, and protected from direct impingement of the exhaust gases and the particulates therein by the shield 41h.

The embodiment of the invention discloses in FIG. 13 has the following advantage: the resistors 17 and 19 remain hotter in cold exhaust streams thereby offering better response, the lower thermal mass allows greatly reduced heat-up times, and the tip length can be changed merely by changing the length of the second insulator 13h and the platinum leads 21. While the upper part of the sensor of FIG. 13 is depicted as being the same as that shown in FIG. 1, it is to be understood that the arrangements for this portion of sensor shown in the other figures may be substituted for the configuration shown. In fact, it is to be understood that individual features from the various embodiments of the invention may be combined to produce other configurations not specifically illustrated.

It can be seen from the above that various modifications can be made to the invention and that selected features from different embodiments of the invention can be combined; however, these embodiments are meant to be illustrative only and not limiting since it will be appreciated by those skilled in the art that other modifications fully within the scope of the invention can also be made. Accordingly, the invention is to be given the full scope of the appended claims, including any and all equivalents thereof.

We claim:

1. An oxygen sensor particularly adapted for detecting the oxygen concentration in the exhaust gas of an internal combustion engine exhaust system comprising:

a first generally cylindrical electrical insulator having an axial bore extending therethrough with one end of said bore being counterbored for a substantial distance, said first insulator having a radially enlarged outer portion spaced from the second end thereof;

an annular connector shell which fits over and engages said radially enlarged portion of said first insulator and is adapted to be secured in a wall of the exhaust system with the second end of said first insulator disposed in the exhaust stream;

a second electrical insulator of substantially uniform circular cross-section disposed in said bore in the first insulator and with a first end thereof adjacent the counterbore, said second insulator having at least two longitudinal bores therethrough;

a means for retaining said second electrical insulator in said bore in the first insulator;

a detector element having at least two electrical leads, said element being disposed adjacent the second end of the first insulator with the electrical leads thereof extending through the longitudinal bores in said second insulator into the counterbore in the first insulator;

at least two terminals disposed longitudinally in the counterbore in the first insulator with an outer end extending axially beyond the first end of the first insulator, said electrical leads each being electrically connected to the inner end of one of said terminals; and electrically nonconductive means for supporting the terminals in place in the counterbore.

2. The sensor of claim 1 wherein said detector element comprises a first element having an electrical resistance characteristic which varies as a function of temperature and the presence of gaseous oxygen to which the element is exposed, and a second element having an electrical resistance characteristic which varies with temperature in a manner similar to that of the first element but does not vary as a function of gaseous oxygen present, wherein each said element is provided with two electrical leads, wherein said second insulator is provided with three longitudinal holes, one for one lead from each element and one for a common lead from the two elements, and wherein three terminals are provided, one for each of the leads extending through the three longitudinal bores in the second insulator.

3. The sensor of claim 1 wherein the electrically nonconductive means for supporting said terminals in the counterbore in the first insulator comprises a sealer which hardens in place.

4. The sensor of claim 3 wherein the counterbore in the first insulator includes at least two terminal bores offset radially from but partially radially intersecting said axial bore extending through said first insulator, one of said terminals being disposed in each of said terminal bores and being retained therein by the seal.

5. The sensor of claim 1 wherein the electrically nonconductive means for supporting said terminals in the counterbore in the first insulator comprises a third cylindrical electrical insulator having at least two longitudinal bores therethrough, said third insulator being disposed in the counterbore in said first insulator and said terminals being disposed in the longitudinal bores of the third insulator.

6. The sensor of claim 5 wherein said terminals have radially enlarged inner ends larger in diameter than the longitudinal bores in said third insulator.

7. The sensor of claim 5 wherein said annular shell extends axially to the first end of said first insulator and then radially inward over at least the peripheral edge of said third insulator to retain the same in place.

8. The sensor of claim 1 including a cup-shaped shield with a perforated bottom which fits over the second end of said first insulator and said detector element.

9. The sensor of claim 8 wherein the sidewall of said cup-shaped shield extends under the edge of the annular connector shell and is clamped in place thereby.

10. The sensor of claim 1 wherein said means for retaining said second electrical insulator in said bore in the first insulator is a radial inwardly directed flange extending into said bore at the second end of the first insulator and wherein said detector element is disposed in the aperture formed by said flange.

11. The sensor of claim 10 wherein a perforated plate is inserted in the aperture formed by the radial inwardly directed flange formed on the second end of said first insulator.

12. The sensor of claim 10 wherein the radial inwardly directed flange is stepped radially inward and terminates in an axially outwardly extending portion forming a narrow inlet.

13. The sensor of claim 1 wherein said means for retaining said second electrical insualtor in said bore in the first insulator is a radial outwardly directed flange affixed to the first end of said second insulator which flange seats in said counterbore in the first insulator.

14. The sensor of claim 13 wherein the second insulator extends for a substantial distance beyond the second end of said first insulator.

15. The sensor of claim 14 including a cup-shaped shield having openings therein which fits over the second end of said second insulator with the lip of said cup clamped between the exterior of the first insulator and said annular connector shell.

16. The sensor of claim 13 wherein said radial outwardly directed flange comprises a ceramic ring cemented to the first end of the said second insulator.

17. The sensor of claim 13 wherein said radial outwardly directed flange comprises a ring of refractory cement deposited on the first end of said second insulator.

18. The sensor of claim 13 wherein said second insulator is composed of a ceramic material and wherein said radial outwardly directed flange comprises a ring of the same ceramic material as the first insulator applied to the first end of the second insulator while in the green state and fired in place.

19. The sensor of claim 17 wherein the second insulator is in the green state when the flange of green ceramic material is applied thereto and then the resulting assembly is fired.

20. The sensor of claim 1 including keying means for assuring that the terminals may be mated properly with a cooperating plug.

21. The sensor of claim 2 wherein said first element comprising a titania resistor and said second element comprises a compensating resistor.

* * * * *